United States Patent
Cai et al.

(10) Patent No.: US 7,946,988 B2
(45) Date of Patent: May 24, 2011

(54) MEDICAL DIAGNOSTIC ULTRASOUND CONTRAST AGENT DESTRUCTION WITH REDUCED BIOLOGICAL EFFECT

(75) Inventors: Anming He Cai, San Jose, CA (US); Lewis J. Thomas, Palo Alto, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1453 days.

(21) Appl. No.: 11/302,567

(22) Filed: Dec. 13, 2005

(65) Prior Publication Data
US 2007/0167799 A1 Jul. 19, 2007

(51) Int. Cl.
*A61B 8/00* (2006.01)
(52) U.S. Cl. ......... 600/442; 600/437; 600/407; 600/458
(58) Field of Classification Search ........................ None
See application file for complete search history.

(56) References Cited

U.S. PATENT DOCUMENTS

| | | | |
|---|---|---|---|
| 5,675,554 A | 10/1997 | Cole et al. | |
| 5,685,308 A | 11/1997 | Wright et al. | |
| 5,827,188 A | 10/1998 | Wright et al. | |
| 5,856,955 A | 1/1999 | Cole et al. | |
| 5,882,307 A | 3/1999 | Wright et al. | |
| 6,213,947 B1 * | 4/2001 | Phillips | 600/443 |
| 6,241,674 B1 | 6/2001 | Phillips et al. | |
| 6,340,348 B1 * | 1/2002 | Krishnan et al. | 600/447 |
| 6,461,303 B2 * | 10/2002 | Angelsen | 600/458 |
| 6,494,841 B1 | 12/2002 | Thomas et al. | |
| 6,558,328 B2 | 5/2003 | Chiao et al. | |
| 6,632,177 B1 | 10/2003 | Phillips et al. | |
| 2003/0092991 A1 * | 5/2003 | Sehgal | 600/458 |

OTHER PUBLICATIONS

"Premature ventricular contractions during triggered imaging with ultrasound contrast," by van Der Wouw PA, Brauns AC, Bailey SE, Powers JE and Wilde AA; Department of Cardiology, Academic Medical Center, Amsterdam, The Netherlands; <http://www.ncbi.nlm.nih.gov/entrez/query.fcgi?cmd=Retrieve&db=pubmed&dopt=Abstract&list_uids=10756246&query_hl=4> printed Nov. 28, 2005; 2 pages (Abstract)—dated as J. Am Soc Echocardiography, Apr. 2000; 13(4):288-94.

"Destruction of Contrast Microbubbles by Ultrasound Effects on Myocardial Function, Coronary Perfusion Pressure, and Microvascular Integrity," by Taniyel Ay et al.; Circulation, 2001; 104, Jul. 24, 2001 pp. 461-466.

* cited by examiner

*Primary Examiner* — Tse Chen
*Assistant Examiner* — Joel F Brutus

(57) ABSTRACT

Contrast agent destruction transmissions have reduced biological effect in medical diagnostic ultrasound. Ramping-up amplitude and/or ramping-down frequency reduce biological effect. The amplitude ramps up linearly or non-linearly. The change in amplitude or frequency occurs over a single waveform or over a sequence of separate transmissions. An envelope of the single waveform or the sequence of separate transmissions has a non-uniform, asymmetrical, symmetrical, rectangular or other shape. For example, the frequency ramp-down is provided with a non-Gaussian envelope. The amplitude ramp-up or frequency ramp-down is a progressively increasing destructive characteristic or ability, destroying contrast agent at different regions relative to focal regions with a minimum of acoustic energy.

21 Claims, 1 Drawing Sheet

MEDICAL DIAGNOSTIC ULTRASOUND CONTRAST AGENT DESTRUCTION WITH REDUCED BIOLOGICAL EFFECT

BACKGROUND

The present embodiments relate to contrast agent destruction or imaging with ultrasound. In particular, medical diagnostic ultrasound destroys, with reduced biological effect, contrast agents.

Perfusion assessment uses contrast agents assisted ultrasound imaging of various organs. Contrast agents are typically microbubbles that may be destroyed by ultrasound energy. For perfusion assessment, an ultrasound destruction frame cleans-up or destroys microbubbles before imaging microbubble accumulation (wash-in) in the object of interest over time. Employing transmit pulses with higher peak-negative pressure and lower frequencies more likely destroys more microbubbles.

However, the higher pressure and lower frequency may cause biological effects since some of the bubbles grow bigger before breaking. Negative transient biological effects on myocardial function, coronary perfusion pressure, and microvascular integrity can occur during ultrasound contrast agent imaging within the normal FDA diagnostic mechanical index (MI) and thermal limits. For example, areas of epicardial hemorrhage appear in rabbit hearts exposed to contrast agents and ultrasound energy with a MI of 1.6 at harmonic imaging frequencies of 1.8 MHz/3.6 MHz. Micrographs show capillary rupture, extravasation of red blood cells into interstitial space and distribution of peroxidase activity in the myocardium covered by the ultrasound beam elevation and exposed to the MI of 1.6. Micrographs show normal microscopic appearance and an absence of significant peroxidase activity in myocardial regions located outside the beam elevation. Ultrasound with a 1.6 MI without contrast agents rupture much less than 1% of capillaries, but with contrast agents may rupture over 3% of capillaries. Ultrasound at 1.0 MI with contrast agents may rupture over 1% of capillaries.

To avoid ruptures or other biological effects, contrast agents are imaged with low MI, such as transmitting ultrasound energy with less than 0.6 MI. U.S. Pat. Nos. 6,494,841 and 6,632,177, the disclosures of which are incorporated herein by reference, show techniques for low MI contrast agent imaging. However, the destruction of contrast agents may be desired or unavoidable in some ultrasound imaging methods.

BRIEF SUMMARY

By way of introduction, the preferred embodiments described below include methods, instructions and systems for contrast agent destruction with reduced biological effect in medical diagnostic ultrasound. Ramping-up amplitude and/or ramping-down frequency reduce biological effect. The amplitude ramps up linearly or non-linearly. The change in amplitude or frequency occurs over a single waveform or over a sequence of separate transmissions. An envelope of the single waveform or the sequence of separate transmissions has a non-uniform, asymmetrical, symmetrical, rectangular or other shape. For example, the frequency ramp-down is provided with a non-Gaussian envelope. The amplitude ramp-up or frequency ramp-down is a progressively increasing destructive characteristic, destroying contrast agent at different regions relative to focal regions with a minimum of acoustic energy.

In a first aspect, a method for contrast agent destruction reduces biological effects in medical diagnostic ultrasound. Acoustic energy is transmitted into a region with contrast agents with amplitudes substantially linearly increasing as a function of time.

In a second aspect, a method for contrast agent destruction reduces biological effects in medical diagnostic ultrasound. Acoustic energy is transmitted into a region with contrast agents with frequency decreasing as a function of time. The acoustic energy has an envelope characteristic of substantially rectangular, linearly increasing, different rate of change in a first half than a second half, abrupt transition, or combinations thereof.

In a third aspect, a method for contrast agent destruction reduces biological effects in medical diagnostic ultrasound. Acoustic energy is transmitted into a region with contrast agents. The acoustic energy has a progressively increasing destructive characteristic with a more rapid decrease in destruction characteristic.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A single ultrasound transmit waveform or multiple ultrasound transmit sequences clean up or destroy contrast agent microbubbles in the imaging field. The waveforms or transmit sequences are adapted to minimize biologic effects. Single waveforms include amplitude ramp-up or frequency ramp-down. Multiple transmissions are sequenced from low amplitude to high amplitude, or from high frequency to low frequency. The frequency or amplitude changes over time may break microbubbles with a reduced biologic impact.

Figure 1:
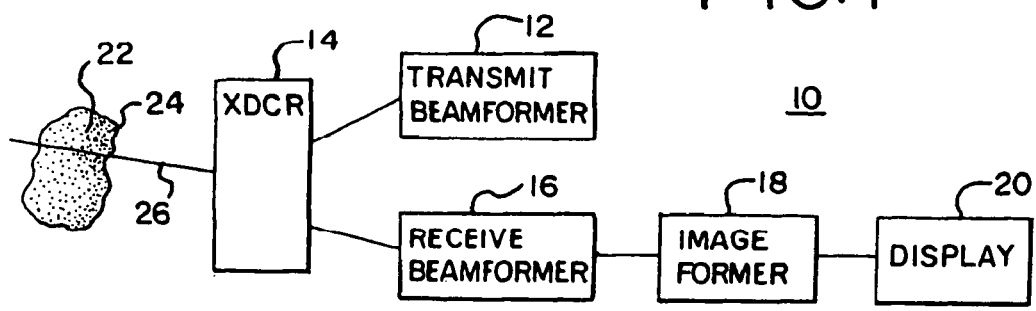
FIG. 1 is a block diagram of one embodiment of an ultrasound system for reducing biological effects of contrast agent destruction.

FIG. 1 shows one embodiment of an ultrasound system 10 for reducing biological effects from destruction of contrast agents. The system 10 is a cart based, portable, handheld or other medical diagnostic ultrasound system. In alternative embodiments, the system 10 is an ultrasound therapeutic system. The system 10 includes a transmit beamformer 12, a transducer 14, a receive beamformer 16, an image former 18 and a display 20. Additional, different or fewer components may be provided. For example, an EKG trigger input is provided for synchronizing cardiac contrast agent imaging with transmissions by the transmit beamformer 12. As another example, the transmit beamformer 12 and transducer 14 are provided with or without any of the other components.

The transmit beamformer 12 includes one or more waveform generators, memories, pulsers, high voltage switches, phase rotators, delays, amplifiers, digital circuits, analog circuits, combinations thereof or other now known or later developed transmit beamformer components. In one embodiment, the transmit beamformer 12 is a programmable waveform beamformer, such as disclosed in U.S. Pat. Nos. 5,856,955 or 5,675,554, the disclosures of which are incorporated herein by reference. Sinusoidal, square wave, unipolar, or bipolar with any desired envelope may be generated using samples from a memory and a digital-to-analog converter. In another embodiment, the transmit beamformer 12 is a programmable waveform beamformer for coded excitations, such as disclosed in U.S. Pat. Nos. 6,213,947 or 6,241,674. In another embodiment, the transmit beamformer 12 is a pulser or switch based beamformer for generating unipolar or bipolar square waves. An amplifier or voltage source connections provide for different amplitudes. Switch frequency provided for waveform frequency. Other now known or later developed beamformers may be used.

The transmit beamformer 12 generates waveforms in different channels. The waveforms are coded or not coded. The transmit beamformer 12 applies delay and apodization profiles to waveforms generated in different channels. The profiles focus the responsive acoustic energy along one or more scan lines 26 in a given transmission. Alternatively, a plane, diverging, unfocused, or defocused wavefront is generated. The wavefront may be steered or unsteered. A single channel may be used.

The transducer 14 includes one or more elements. The elements are arrayed as a one dimensional, multi-dimensional (1.25, 1.5, 1.75, 2D), annular or other distribution. The elements are piezoelectric or capacitive membrane based elements.

In response to electrical energy from the transmit beamformer 12, the elements of the transducer 14 generate acoustic waveforms. The acoustic waveforms insonify the scan line 26 through a region 24 including contrast agents 22. Any contrast agents 22 may be used, including inhomogeneous or homogeneous microspheres. The contrast agents may carry or include a drug, for targeted delivery of the drug to the region 24. Alternatively, the contrast agents are free of drugs. By generating waveforms or sequences of transmissions with progressively increasing amplitude and/or decreasing frequency, the transmit beamformer 12 and transducer 14 may reduces biological effects of destruction of contrast agents 22. For example, relative high MI acoustic energy, such as at 1.0 or higher (e.g., 1.6), is transmitted. By changing amplitude or frequency as a function of time, contrast agents in different locations may be destroyed at different times, but without or with less expansion of the contrast agents prior to destruction. The lower amplitude or higher frequency energy may destroy some agents and not others. The shift in amplitude or frequency may destroy other contrast agents after previous destruction, limiting biological effects from destruction of contrast agents from relatively high energy.

The transducer 14 may be used to receive acoustic echoes responsive to the transmissions. For example, echoes responsive to every transmission are received. As another example, echoes responsive to some of the transmissions are not used, but other echoes are received. For receiving acoustic echoes, the acoustic energy is converted to electrical signals by each element of a receive aperture.

The receive beamformer 16 includes one or more amplifiers, delays, phase rotators, filters, summers, mixers, demodulators, analog-to-digital converters, digital circuits, analog circuits, combinations thereof or other now known or later developed receive beamformer components. In one embodiment, the receive beamformer 16 is a receive beamformer disclosed in U.S. Pat. Nos. 5,685,308, 5,882,307 or 5,827,188, the disclosures of which are incorporated herein by reference. In another embodiment, the receive beamformer 16 includes a decoding receiver for applying a pulse compression function corresponding to a transmit code, such as disclosed in U.S. Pat. Nos. 6,213,947 or 6,241,674, the disclosures of which are incorporated herein by reference. Receive beamformers 16 for receiving fundamental or harmonic information may be used. For example, the receive beamformer 16 includes a high pass or band pass filter for receiving at a second harmonic of a fundamental transmit frequency. Information at a fundament or transmit frequency band may also or alternatively be used. As another example, the receive beamformer 16 includes a filter, multipliers, summer or subtractors for combining data responsive to different transmit waveforms to isolate information with a desired characteristic, such as even harmonic information. Receive beamformers 16 for receiving echoes responsive to plane, broad or diverging wavefronts may be used, such as parallel receive beamformers or Fourier transform processors. Other receive beamformers or no receive beamformer may be used.

The image former 18 is a detector and scan converter. The image former 18 receives beamformed signals and outputs data for an image. The image is displayed on the display 20. The image former 18 may form one, two or three dimensional images or representations.

Figure 2:
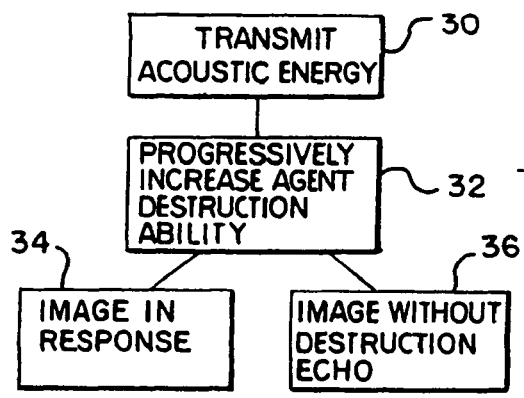
FIG. 2 is a flow chart diagram of one embodiment of a method for contrast agent destruction with reduced biological effect in medical diagnostic ultrasound.

FIG. 2 shows method for contrast agent destruction with reduced biological effect in medical diagnostic ultrasound. The method is implemented with the system 10 of FIG. 1 or a different system. Additional, different or fewer acts may be provided, such as performing the transmitting of act 30 with or without any of the other acts.

In act 30, acoustic energy is transmitted. The acoustic energy is from a point source or an array. A converging, plane (infinite focus), or a diverging focus may be used. The acoustic energy propagates into a region with contrast agents. Multiple transmissions along a same, adjacent or different scan lines may be used. The region is an area or a volume along a scan line or propagation path. The region may be a region of interest, an organ, a portion of an organ, a fluid cavity, a vessel or other location. The acoustic energy has a relatively high mechanical index at an elevation focal point, a steered focal point or other location. Relatively high is 1.0 or higher, but lower mechanical index values may be used. The acoustic energy is within any required limits, such as being 1.6 or less, but may exceed the limits if allowable.

Figure 3:
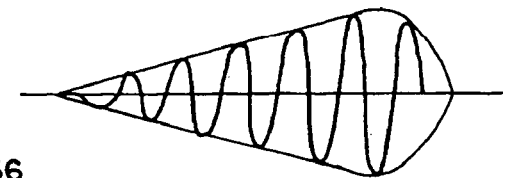
FIG. 3 is a graphical representation of a waveform with a linearly increasing amplitude characteristic in one embodiment.
Figure 4:
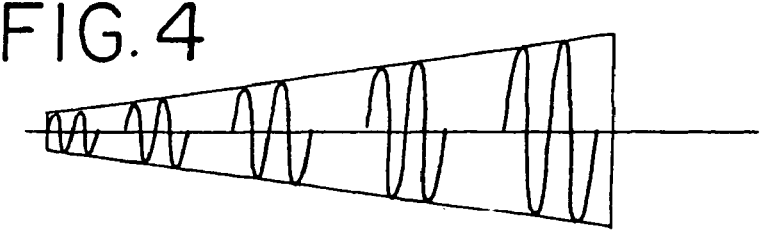
FIG. 4 is a graphical representation of a sequence of transmissions with linearly increasing amplitudes in one embodiment.

In act 32, the transmission has a progressively increasing destructive characteristic or ability. The characteristic increases over at least three iterations. The iterations occur over a single transmit event, such as within one or more transmit waveforms. FIG. 3 shows increasing amplitude of pulses or cycles within a single waveform. Alternatively or additionally, the iterations occur over a sequence of transmissions. FIG. 4 shows increasing amplitude over five sequential transmissions. In one embodiment, the sequential transmissions are used for destruction of contrast agents during a perfusion study, such as described in U.S. Pat. No. 6,340,348, the disclosure of which is incorporated herein by reference. In other embodiments, the sequential transmissions are used for acquiring multiple samples along a same or adjacent scan lines for a single image or for different images (i.e., sequential scans). Combinations of changing characteristic within a waveform and over a sequence of transmissions may be used.

The transmission has the progressively increasing destructive characteristic or ability with a more rapid decrease in destruction ability. The transmission destroys contrast agents. Once sufficient destruction occurs, the transmission ceases or more rapidly alters characteristics to avoid delay. Progressively more destructive transmissions may break microbubbles with minimal size growth. Only those microbubbles not broken by lower amplitude or higher frequency portion of the transmit pulses are subjected to higher amplitude or lower frequency transmissions. For contrast agent destruction, higher amplitude and lower frequency are typically used due to the elevation non-uniformity of the transmit beam near the mechanical elevation focus.

To avoid or minimize damage, a transmit pulse or a transmit pulse sequence is fired along each ultrasound scan line. The waveform or sequence starts with lower amplitude or high frequency, breaking contrast agents in the shallower field and far field near any focal regions. With gradual amplitude increase or frequency decrease, the destruction field extends to other locations. Each location of destruction is provided by minimal acoustic energy for that location. Increasing destruction characteristics of the transmitted acoustic energy progressively destroy contrast agents in different regions as a function of the distance from any focal points. The proceeding low amplitude or high frequency portion of the acoustic energy may destroy the contrast agents nearer the elevation focus before the arrival of the higher amplitude or low frequency portion for off-elevation focus destruction, avoiding high MI bubble destruction at the location of highest MI.

The ability to destroy contrast agents progressively increases by changes in the characteristics of the acoustic energy. One such characteristic is amplitude. The amplitude of the waveform or sequence increases as a function of time. Non-linear or linear increases may be used. In one embodiment, a substantially linear increase is used for more even dispersal or progression of destruction. FIGS. 3 and 4 show substantially linear increases in amplitude. FIG. 3 shows an abrupt drop off from the linear increase at an end of a waveform. Substantially accounts for one or more pulses or cycles deviating from the linear increase, such as the last cycle of the multi-cycle waveform shown in FIG. 3. In FIG. 3, the linear ramp-up begins near a zero value. As shown in FIG. 4, the linear ramp-up may begin at a non-zero value, such as a value for destruction of contrast agents at a focal region while minimizing excess acoustic energy. Repetition of the waveform of FIG. 3 or sequence of transmissions of FIG. 4 may be provided. Within the waveform or each sequence, the amplitude increase is substantially linear. Greater or lesser rates of increase may be used.

By adding a gradual amplitude ramp-up, the maximal bubble size before collapsing is reduced, especially around higher intensity areas in the transmit beam path, minimizing any biological effect. Different changes in amplitude may be used, such as using more linear change for destruction only transmissions and a less linear change for transmissions also used to generate image information. Any number of cycles may be used, such as 3-10 cycles. In one example, a 1.75 MHz waveform of 6.25 cycles with a linear ramp-up and sudden or abrupt end of the waveform (i.e., little or no ramp-down) progressively destroys 0.7 µm Definity® microspheres. The maximal microsphere size for a rectangular envelope is about 2.3 times larger than with a linear ramp-up.

Another characteristic of the acoustic energy for progressively increasing the ability to destroy contrast agents is frequency. The frequency of the transmitting acoustic energy decreases as a function of time. The frequency range may be the bandwidth of the transducer or less, such as a chirp ratio of 8. The frequency change is linear or non-linear. Any number of cycles, such as 3 or more cycles may be used. In one embodiment, a chirp with a center frequency of 1.75 MHz and 50% bandwidth is used with an MI of 1.2. The chirp has a Gaussian envelope, but other envelopes may be used. For 0.7 µm Definity® microspheres and a time-bandwidth of 4 or 2, the maximum microsphere radius before destruction may be less than without the frequency change. For an MI of about 1.2, the maximum microsphere radius may be about 2.5 times less.

In one embodiment, a sequence of transmissions with progressively lower frequencies is transmitted. The change in frequency between transmissions of the sequence is linear or non-linear. One or more subsequent transmissions may have an increasing frequency. Each transmission in the sequence has a Gaussian, rectangular or other envelope. The envelope for the sequence is rectangular or has another shape, such as a linearly decreasing or increasing amplitude. Pulses or transmissions within the sequence may have the same or different shapes (envelopes), frequencies or focus depths.

Figure 5:
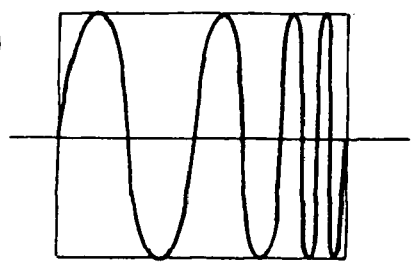
FIG. 5 is a graphical representation of one embodiment of a waveform with a frequency ramp-down and a rectangular envelope.

FIG. 5 shows a waveform with a decreasing frequency. In other embodiments, sequential transmissions each have waveforms at a constant frequency, but lower frequencies are used for later occurring transmissions of the sequence. For high-MI imaging, frequency down-chirp changes the frequency from higher to lower, possibly avoiding more violent bubble collapse from high-MI transmissions. With receive frequency de-chirping or decoding, the axial resolution may be restored.

The transmission has an envelope. Any envelope may be used. For example, the envelope is characterized by an abrupt transition. FIGS. 3-5 show an abrupt transition. The envelope transitions at an end to a zero value. Abrupt transitions to non-zero values, within the envelope, at a beginning of the envelope or combinations thereof may be used. FIG. 5 shows a rectangular envelope. FIGS. 3 and 4 show linearly increasing envelopes. Asymmetric envelopes may be used, such as envelopes with a rate of change in a first half greater than in a second half. For example, a Gaussian envelope is altered to provide a more gradual or progressive increase and a more rapid decrease of the envelope. Other envelopes, such as Hamming or Gaussian may be used. Combinations of envelope characteristics may be used.

The envelope is for a single waveform or over a sequence of transmissions. For example, subsequent ones of the transmissions of a sequence have (a) an amplitude that is a substantially linear increase from a previous one of the transmissions (see FIG. 4). The amplitude ramps-up from an initial or starting point to a final or other point in the envelope. As another example, a non-Gaussian envelope, such as the rectangular (see FIG. 5), linear increase with an abrupt transition (see FIGS. 3-5), or an asymmetric envelope are provided for amplitude of the frequency ramp-down transmission. In yet another example, waveforms or pulse trains of a sequence of transmissions each have a same or different envelope (e.g., Gaussian or rectangular) and the envelope of the sequence varies or is rectangular.

In act 34, images are generated responsive to the transmission. For example, loss-of-correlation or other contrast agent imaging responds to the transmission of contrast agent destructive energy. Echoes from the transmission are received and used for determining image values. For coded transmissions, the received echo signals are decoded.

Act 36 is an alternative to act 34. Images are generated after the transmission without receiving echoes in response to one or more transmissions. Some multi-path reverberations may exist, but the received signals are primarily responsive to a different or later transmission. In perfusion studies, the transmission of act 30 cleans-out or destroys many or most contrast agents before low-MI imaging of the contrast-agent for wash-in and/or washout analysis. As shown in U.S. Pat. No. 6,340,348, the disclosure of which is incorporated herein by reference, destruction frames are fired to clear the bubbles. The region is imaged after transmitting the destruction frames without receiving echoes for imaging in response to the transmitted destruction frames. The later imaging is performed with high or low MI transmissions.

In other embodiments, some of the transmissions with a characteristic having an increasing ability to destroy contrast agents are used for imaging and some are not. The transmissions for imaging are the same or different from transmissions not for imaging, such as both having an increasing ability to destroy contrast agents but by a different amount or rate.

The acts 30, 32, 34 and/or 36 are implemented by hardware, software or combinations thereof. In one embodiment, instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for contrast agent destruction with reduced biological effect in medical diagnostic ultrasound, the method comprising the act of transmitting with a waveform or a sequence of transmissions having an envelope characteristic of a different rate of change in a first half than a second half, abrupt transition, or combinations thereof, into a region with contrast agents, acoustic energy with amplitudes substantially linearly increasing as a function of time, the linear increase being substantially linear across at least five sequential iterations of amplitude increases, wherein the envelope characteristic has the substantially linearly increasing amplitudes with an abrupt transition at an end of the envelope.

2. A method for contrast agent destruction with reduced biological effect in medical diagnostic ultrasound, the method comprising the act of transmitting with frequency decreasing as a function of time, into a region with contrast agents, acoustic energy with amplitudes substantially linearly increasing as a function of time, the linear increase being substantially linear across at least five sequential iterations of amplitude increases.

3. A method for contrast agent destruction with reduced biological effect in medical diagnostic ultrasound, the method comprising the act of transmitting, into a region with contrast agents, acoustic energy with waveform frequency decreasing as a function of time, the acoustic energy having an envelope characteristic of substantially rectangular, linearly increasing, different rate of change in a first half than a second half, abrupt transition, or combinations thereof.

4. The method of claim 3 wherein transmitting comprises transmitting with the envelope characteristic of substantially rectangular.

5. The method of claim 3 wherein transmitting comprises transmitting with the envelope characteristic of linearly increasing.

6. The method of claim 3 wherein transmitting comprises transmitting with the envelope characteristic of the different rate of change in the first half than the second half.

7. The method of claim 3 wherein transmitting comprises transmitting with the envelope characteristic of the abrupt transition.

8. The method of claim 3 wherein transmitting comprises transmitting a sequence of transmissions into the region, subsequent ones of the transmissions of the sequence having the waveform frequency that is less than a previous one of the transmissions and a MHz frequency.

9. The method of claim 3 wherein transmitting comprises transmitting a waveform having a frequency ramp down.

10. The method of claim 3 further comprising:
progressively increasing destruction of the contrast agents as a function of the transmitting.

11. The method of claim 3 further comprising:
imaging the region after the transmitting without receiving echoes for imaging in response to the transmitting.

12. The method of claim 3 wherein transmitting comprises transmitting with a mechanical index of at least 1.0.

13. The method of claim 3 further comprising:
imaging as a function of echoes received in response to the transmitting.

14. A method for contrast agent destruction with reduced biological effect in medical diagnostic ultrasound, the method comprising the act of transmitting, into a region with contrast agents, acoustic energy with a progressively increasing destructive characteristic followed by a more rapid decrease in destruction characteristic;
wherein transmitting comprises transmitting a sequence of transmissions into the region, subsequent ones of the transmissions of the sequence having (a) an amplitude that is a substantially linear increase from a previous one of the transmissions, (b) a MHz waveform frequency that is a decrease from the previous one of the transmissions, or combinations thereof.

15. The method of claim 14 wherein transmitting comprises transmitting along a same scan line.

16. The method of claim 14 wherein transmitting comprises transmitting with the progressively increasing destructive characteristic increasing over at least three iterations.

17. The method of claim 14 wherein transmitting comprises transmitting with a sequence of transmissions having an envelope characteristic of a different rate of change in a first half than a second half, abrupt transition, or combinations thereof.

18. The method of claim 14 wherein transmitting comprises ramping up the amplitude, ramping down the MHz waveform frequency, or combinations thereof from an initial transmission of a sequence to a final transmission of the sequence or waveform pulse.

19. The method of claim 14 wherein the increase or the decrease occurs for each subsequent pulse or waveform in a set of pulses or waveform comprising the sequence.

20. The method of claim 14 wherein the sequence comprises a clean-up of the contrast agents prior to imaging contrast agent accumulation, the progressively increasing destructive characteristic operable to more likely destroy contrast agents at a different locations at different times as a function of level of the characteristic and with a bubble size of the contrast agent upon destruction based on the level.

21. A method for contrast agent destruction with reduced biological effect in medical diagnostic ultrasound, the method comprising the act of transmitting, into a region with contrast agents, a sequence of transmissions of acoustic energy, subsequent ones of the transmissions of the sequence having a MHz waveform frequency that is less than a previous one of the transmissions.

* * * * *